United States Patent [19]
Yarwood et al.

[11] Patent Number: 5,827,541
[45] Date of Patent: Oct. 27, 1998

[54] PROCESS FOR PREPARING SOLID PHARMACEUTICAL DOSAGE FORMS OF HYDROPHOBIC SUBSTANCES

[75] Inventors: Richard John Yarwood; Patrick Kearney; Andrew Roy Thompson, all of Wiltshire, United Kingdom

[73] Assignee: R. P. Scherer Corporation, Troy, Mich.

[21] Appl. No.: 663,103

[22] PCT Filed: Oct. 20, 1995

[86] PCT No.: PCT/GB95/02485

§ 371 Date: Jul. 18, 1996

§ 102(e) Date: Jul. 18, 1996

[87] PCT Pub. No.: WO96/13251

PCT Pub. Date: May 9, 1996

[30] Foreign Application Priority Data

Oct. 28, 1994 [GB] United Kingdom ................... 9421836

[51] Int. Cl.[6] ..................................................... A61K 9/14
[52] U.S. Cl. .......................... 424/489; 424/464; 424/480; 424/494
[58] Field of Search ..................................... 424/489, 488, 424/490, 466, 465

[56] References Cited

U.S. PATENT DOCUMENTS 5,456,920  10/1995  Matoba et al. .......................... 424/465
5,587,179  12/1996  Gergely et al. .......................... 424/466

FOREIGN PATENT DOCUMENTS

| 0 159 237 | 10/1985 | European Pat. Off. . |
| 0 450 141 /A1 | 10/1991 | European Pat. Off. . |
| 0 578 823 A1 | 1/1994 | European Pat. Off. . |
| 2 366 835 | 5/1978 | France . |
| 90 05512 | 11/1991 | France . |
| 1 548 022 | 9/1977 | United Kingdom . |
| 2 111 423 | 7/1983 | United Kingdom . |

OTHER PUBLICATIONS

Derwent Abstract of WO 93 JP1631.

*Primary Examiner*—Thurman K. Page
*Assistant Examiner*—William E. Benston, Jr.
*Attorney, Agent, or Firm*—Nixon & Vanderhye P.C.

[57] ABSTRACT

Process for preparing an oral rapidly disintegrating dosage form of a hydrophobic pharmaceutically active substance comprising forming a suspension of the hydrophobic pharmaceutically active substance in a solvent containing a pharmaceutically acceptable surfactant together with a water-soluble or water-dispersible carrier material, forming discrete units of the suspension and removing solvent from the discrete units under conditions whereby a network of the carrier material carrying a dosage of the hydrophobic pharmaceutically active substance is formed.

21 Claims, No Drawings

PROCESS FOR PREPARING SOLID PHARMACEUTICAL DOSAGE FORMS OF HYDROPHOBIC SUBSTANCES

This application is a 371 of PCT/GB95/02485 filed Oct. 20, 1995 published as WO96/13251 May 9, 1996.

The present invention relates to a process for preparing solid pharmaceutical dosage forms and, in particular, to a process for preparing an oral solid rapidly disintegrating dosage form of a pharmaceutically active substance.

Many pharmaceutically active substances are presented for oral administration in the form of tablets, pills or capsules. The tablet, pill or capsule generally has to be swallowed with water so that the pharmaceutically active substance can be absorbed via the gastro-intestinal tract. For some patients swallowing the tablet, pill or capsule is difficult or impossible and this is particularly the case for paediatric patients and geriatic patients. A similar difficulty is often encountered when trying to administer tablets to non-human animals which may be uncooperative in taking tablets, pills or capsules.

Oral solid pharmaceutical dosage forms which rapidly disintegrate in the mouth and methods for their preparation have been proposed in GB-A-1548022 and GB-A-2111423. The solid dosage forms as disclosed comprise an open matrix network carrying the pharmaceutically active substance, the open matrix comprising a water-soluble or water-dispersible carrier material which is inert towards the pharmaceutically active substance. The solid dosage forms are prepared by the sublimation or removal of solvent from a solution or suspension comprising the pharmaceutically active substance and the carrier material. Sublimation or removal of solvent is preferably carried out by freeze drying.

Other methods for the preparation of oral solid pharmaceutical dosage forms which rapidly disintegrate in the mouth are disclosed in U.S. Pat. No. 5,039,540, U.S. Pat. No. 5,120,549, U.S. Pat. No. 5,330,763, PCT/JP93/01631 and PCT/US93/12566.

The solid dosage forms which are produced by these various methods rapidly disintegrate on being placed in the mouth of the patient, thereby delivering the desired dose of the pharmaceutically active substance.

The preparation of oral solid rapidly dispersing dosage forms generally involves the formation of a suspension of the drug in water, optionally together with a co-solvent such as alcohol, together with the matrix forming components. For many drugs a homogeneous suspension cannot be prepared due to the hydrophobicity of the drug which causes a stable foam to form during the mixing process which results in a lack of uniformity of content of the drug in the final product. This problem is exacerbated for very fine particles where air entrapment during mixing becomes greater.

We have now developed a process for the preparation of oral solid rapidly disintegrating dosage forms of hydrophobic drugs in which the foregoing problem is overcome.

Accordingly, the present invention provides a process for the preparation of an oral rapidly disintegrating dosage form of a hydrophobic pharmaceutically active substance which process comprises forming a suspension of the hydrophobic pharmaceutically active substance in a solvent containing a pharmaceutically acceptable surfactant together with a water-soluble or water-dispersible carrier material, forming discrete units of the suspension and removing solvent from the discrete units under conditions whereby a network of the carrier material carrying a dosage of the hydrophobic pharmaceutically active substance is formed.

By the term "rapidly disintegrating" as used herein is meant that the solid dosage form will disintegrate in water at 37° C. in 60 seconds or less, preferably 5 to 10 seconds or less when tested by the following procedure which is analogous to the Disintegration Test for Tablets, B.P. 1973 and which is described in British Patent No. 1548022:

Apparatus

A glass or suitable plastic tube 80 to 100 mm long, with an internal diameter of about 28 mm and an external diameter of 30 to 31 mm, and fitted at the lower end, so as to form a basket, with a disc of rustproof wire gauze complying with the requirements for a No. 1.70 sieve (B.P. 1973 page A136).

A glass cylinder with a flat base and an internal diameter of about 45 mm containing water and not less than 15 cm deep at a temperature between 36° and 38° C.

The basket is suspended centrally in the cylinder in such a way that it can be raised and lowered repeatedly in a uniform manner so that at the highest position the gauze just breaks the surface of the water and at the lowest position the upper rim of the basket just remains clear of the water.

Method

Place one shaped article in the basket and raise and lower it in such a manner that the complete up and down movement is repeated at a rate equivalent to thirty times a minute. The shaped articles are disintegrated when no particle remains above the gauze which would not readily pass through it.

On oral administration of the solid dosage form of the invention to a patient the pharmaceutical dosage form rapidly disintegrates in the mouth.

The process for the preparation of oral rapidly disintegrating solid dosage forms in accordance with the present invention enables hydrophobic pharmaceutically active substances to be presented for administration in this form.

The incorporation of the surfactant into the solvent used during the preparation of the suspension of the drug prevents the formation of a foam on mixing and ensures uniformity of the content of the drug in the dosage units and thus overcomes problems associated with air entrapment.

Furthermore, hydrophobic pharmaceutically active substances do not generally disperse easily and rapidly in the mouth and the addition of the surfactant during the processing of the drug improves the dispersion of the dosage units formed in the process of the invention within the mouth. Furthermore, for some hydrophobic pharmaceutically active substances the addition of the surfactant during processing improves the bioavailability of the product due to improved wetting of the pharmaceutically active substance leading to further dissolution and absorption.

Any surfactant which fulfils the requirement of pharmaceutical acceptability may be used in the invention. Particularly suitable surfactants for use in the present invention are the Poloxamers which are α-hydro-co-hydroxypoly (oxyethylene)-poly(oxyethylene)block copolymers and polysorbates which are polyoxyethylene derivatives of sorbitan esters. Since the surfactant will remain in the finished dosage form of the product it is important that it has an acceptable taste.

The process of the present invention is of particular use for the preparation of oral solid rapidly disintegrating dosage forms of hydrophobic pharmaceutically active agents which have a very small particle size since the ease of wetting becomes more difficult in the absence of a surfactant as the particle size decreases and the air entrapment during mixing in the absence of a surfactant becomes greater. The present invention is thus of particular utility in preparing solid rapidly disintegrating dosage forms of hydrophobic pharmaceutically active agents having an average particle size of less than less than 50 μm, generally of less than 20 μm, more preferably less than 10 μm.

Hydrophobic pharmaceutically active agents which may be processed according to the present invention include domperidone and bromocriptine mesylate.

The discrete units of the suspension may be in the form of liquid units, for example contained within the pockets of a suitable mould, solid units, for example frozen units, or gelled units where the carrier material readily forms a gel.

The removal of solvent from the discrete units of the suspension comprising the hydrophobic pharmaceutically active substance and a water-soluble or water-dispersible carrier material is carried out by techniques well known to those skilled in the art.

When the discrete units are in liquid form they will generally be frozen or gelled prior to drying.

The liquid suspension which may be contained within the pockets of a suitable mould is frozen, for example by passing a gaseous cooling medium, such as liquid nitrogen over the mould, or by inserting the mould into a nitrogen spray freezing chamber, or cooling by passing the mould over a cold surface. Once the dosage forms have been frozen, the mould may be stored in a cold store, prior to drying. Frozen discrete units may be dried by freeze drying according to techniques which are well known in the art. The solvent is sublimed in a freeze drying process under a reduced pressure which transforms the solid solvent directly into a vapour. The freeze drying process will generally be carried out in a freeze drying chamber typically operating under a vacuum of 0.1 to 1.0 mBar for a period of time of from 180 to 500 minutes.

Alternatively, frozen discrete units may be dried by a process as described in U.S. Pat. Nos. 5,120,549 and 5,330,763. In this method the pharmaceutically active substance and carrier material dispersed in a first solvent is solidified and the solidified matrix is subsequently contacted with a second solvent that is substantially miscible with the first solvent at a temperature lower than the solidification point of the first solvent, the matrix component being substantially insoluble in the second solvent, the first solvent thereby being removed from the matrix.

Another alternative process for drying frozen discrete units is described in WO94/14422. In this process the solvent is removed under conditions whereby the solvent is evaporatated from the solid through the liquid phase to a gas, rather than subliming from a solid to a gas as in lyophilization. This is achieved by vacuum drying at a temperature below the equilibrium freezing point of the composition at which point the solvent (such as water) changes phase.

When the discrete units are gelled units, any drying methods can be used which do not affect the properties of the preparations. For example, drying may be carried out at decreased pressure, or by forced-air drying. Drying at decreased pressure is preferably carried out at a temperature of from 25° to 35° C. under a vacuum of −750 mm Hg or less, for 2 to 5 hours, whilst drying using forced-air drying is preferably carried out at a temperature of from 3° to 15° C. for 1 to 6 days.

The solvent used in forming the suspension of the pharmaceutically active substance is preferably water but it may be admixed with a co-solvent, such as alcohol, if desired.

The carrier material which is used to form the network containing the pharmaceutically active substance may be any water-soluble or water-dispersible material that is pharmaceutically acceptable, inert to the pharmaceutically active substance and which is capable of forming a rapidly disintegrating network. The preferred carrier material for use in the present invention is gelatin, preferably pharmaceutical grade gelatin.

Other materials may also be used, for example hydrolysed dextrose, dextran, dextrin, maltodextrin, alginates, hydroxyethylcellulose, sodium carboxymethylcellulose, microcrystalline cellulose, corn-syrup solids, pectin, carrogeenan, agar, chitosan, locust bean gum, xanthan gum, guar gum, acacia gum, tragacanth, konjac fluor, rice flour, wheat gluten, sodium starch glycolate, soy fibre protein, potato protein, papain, horse radish peroxidase, glycine or mannitol.

The suspension prepared according to the process of the present invention is preferably formed into discrete units by introduction into a mould which preferably comprises a plurality of depressions, each depression being of the desired shape and size for the oral dosage form product. The mould preferably comprises a plurality of depressions formed in a sheet of a filmic material which may be similar to the material employed conventionally in the blister packaging of pharmaceuticals. A particularly preferred filmic material for use as a mould in the present invention is described in WO94/12142. The desired quantities of the suspension may be filled into the mould using an automatic filling means which delivers a predetermined dose into each of the depressions in the mould.

A covering material may be adhered to the filmic material in the area surrounding the depressions after the removal of solvent from the suspension filling the depressions. The covering sheet is preferably an aluminium foil or aluminium foil laminate which may be adhered to the filmic material around the depressions by, for example a heat sensitive material. The cover sheet may be adhered to the filnic material in a manner such that it can be peeled away by the user to uncover the oral dosage form in the depression in the mould or, alternatively, it may be adapted for the oral dosage formed to be pushed through.

Alternative methods of forming discrete frozen or gelled units of the suspension include solidifying the mixtures in dropwise fashion. For example, the suspension may be passed through one or more holes to form drops, spheres or a spray of small particles which can be solidified by passage through a cold gas or liquid, for example liquid nitrogen. Alternatively, the drops, spheres or spray may be solidified by contact with a chilled liquid which is immiscible with the suspension and which has a density such that the drops either fall through the immiscible liquid as they solidify, or float on the surface of the immiscible liquid.

The suspension prepared in accordance with the process of the present invention may also contain other additional ingredients such as colouring agents, flavouring agents, sweetening agents or preservatives, or fillers such as mannitol or sorbitol which improve the physical properties of the oral dosage form.

The present invention also includes within its scope the oral solid rapidly disintegrating dosage forms prepared according to the process of the invention.

The present invention will be further described with reference to the following non-limiting Example.

EXAMPLE

Domperidone was formulated in the form of the free base into an oral rapidly disintegrating dosage form using the following ingredients.

| | |
|---|---|
| Domperidone microfine average particle size less than 50 μm | 10.000 mg |
| Gelatin | 5.513 mg |
| Mannitol | 4.136 mg |
| Aspartame | 0.75 mg |
| Mint flavour | 0.30 mg |
| Poloxamer 188 | 1.125 mg |
| Purified water | |

A solution containing the gelatin, mannitol and Poloxamer 188 was prepared and to this were added the aspartame and mint flavouring. Aliquots of the resulting solution were added to the domperidone powder and a paste formed on stirring. The remainder of the solution was added and a homogeneous suspension was obtained. The suspension was dispensed in 150 mg aliquots into the pockets of a blister pack, frozen and dried to produce the final dosage form.

The bioavailability of the domperidone final dosage form finished product was equivalent to that of a compressed tablet form containing the same quantity of domperidone. The bioavalability of a similar oral rapidly disintegrated product prepared without the Poloxamer surfactant was not, however, equivalent to that of the compressed tablet.

We claim:

1. A process for the preparation of an oral rapidly disintegrating dosage form of a hydrophobic pharmaceutically active substance which disintegrates in water at 37° C. in 60 seconds or less, which process comprises the steps of:

forming a suspension of the hydrophobic pharmaceutically active substance in a solvent containing a pharmaceutically acceptable surfactant together with a water-soluble or water-dispersible carrier material;

forming discrete units of the suspension; and removing solvent from the discrete units under conditions whereby a network of the carrier material carrying a dosage of the hydrophobic pharmaceutically active substance is formed.

2. A process as claimed in claim 1 wherein the hydrophobic substance is in the form of a powder having an average particle size of less than 50 μm.

3. A process as claimed in claim 2 wherein the hydrophobic substance is in the form of a powder having an average particle size of less than 10 μm.

4. A process as claimed in claim 1 wherein the pharmaceutically acceptable surfactant is a Poloxamer or a polysorbate.

5. A process as claimed in claim 1 wherein the hydrophobic pharmaceutically active substance is domperidone or bromocriptine mesylate.

6. A process as claimed in claim 1 wherein the solvent comprises water.

7. A process as claimed in claim 6 wherein the water contains a co-solvent.

8. A process as claimed in claim 1 wherein the carrier material is gelatin.

9. A process as claimed in claim 1 wherein the discrete units are liquid, frozen or gelled units.

10. A process as claimed in claim 9 wherein the discrete units are formed in a mould comprising a plurality of pockets.

11. A process as claimed in claim 9 wherein the discrete units are liquid units which are frozen prior to removal of the solvent.

12. A process as claimed in claim 9 wherein the units are frozen units and the solvent is removed by freeze drying.

13. A process as claimed in claim 9 wherein the units are frozen units and the solvent is removed by contacting the frozen matrix comprising the first solvent, the pharmaceutically active substance and the carrier material with a second solvent that is substantially miscible with the first solvent at a temperature lower than the solidification point of the first solvent, whereby the first solvent is removed from the matrix.

14. A process as claimed in claim 9 wherein the units are frozen units and the solvent is removed by vacuum drying under conditions whereby the solvent is evaporated from the frozen units through the liquid phase to a gas.

15. A process as claimed in claim 9 wherein the discrete units are gelled units from which the solvent is removed by drying under decreased pressure or by forced-air drying.

16. A process as claimed in claim 10 wherein the mould comprises one or more depressions in a sheet of a filmic material.

17. A process as claimed in claim 16 wherein a sheet of a covering material is adhered to the filmic material in the area around the depression or depressions after the removal of solvent from the solution or suspension.

18. An oral solid rapidly disintegrating dosage form of a hydrophobic pharmaceutically active substance whenever prepared by a process as claimed in claim 1.

19. An oral solid rapidly disintegrating dosage form as claimed in claim 18 wherein the pharmaceutically active substance is domperidone which is present in the composition in the form of the domperidone free base.

20. An oral solidly rapidly disintegrating dosage form which disintegrates in water at 37° C. in 60 seconds or less comprising domperidone-free base as the pharmaceutically active substance together with a pharmaceutically acceptable surfactant in a network of a water-soluble or water-dispersible carrier material.

21. An oral dosage form as claimed in claim 20 wherein the surfactant is a Poloxamer or a polysorbate.

* * * * *